(12) United States Patent
Skubitz et al.

(10) Patent No.: US 7,797,054 B2
(45) Date of Patent: Sep. 14, 2010

(54) EXPANDABLE SYSTEMS FOR MEDICAL ELECTRICAL STIMULATION

(75) Inventors: Sean P. Skubitz, Forest Lake, MN (US); Stephen L. Bolea, Watertown, MN (US); Paula M. Kaplan, St. Paul, MN (US); Mary M. Morris, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 771 days.

(21) Appl. No.: 11/622,538

(22) Filed: Jan. 12, 2007

(65) Prior Publication Data

US 2008/0172117 A1 Jul. 17, 2008

(51) Int. Cl.
*A61N 1/04* (2006.01)

(52) U.S. Cl. .................. 607/115; 607/116; 607/117; 607/118

(58) Field of Classification Search .......... 607/115–118
See application file for complete search history.

(56) References Cited

U.S. PATENT DOCUMENTS

| 4,519,403 | A | 5/1985 | Dickhundt |
| 6,091,993 | A | 7/2000 | Bouchier et al. |
| 6,142,993 | A | 11/2000 | Whayne et al. |
| 6,205,361 | B1 | 3/2001 | Kuzma et al. |
| 6,254,598 | B1 | 7/2001 | Edwards et al. |
| 6,319,241 | B1 | 11/2001 | King et al. |
| 6,415,187 | B1 | 7/2002 | Kuzma et al. |
| 6,522,932 | B1 | 2/2003 | Kuzma et al. |
| 6,529,779 | B1 | 3/2003 | Sutton |
| 6,697,676 | B2 | 2/2004 | Dahl et al. |
| 7,072,719 | B2 | 7/2006 | Vinup et al. |
| 7,099,718 | B1 | 8/2006 | Thacker et al. |
| 2001/0053885 | A1 | 12/2001 | Gielen et al. |
| 2005/0004639 | A1 | 1/2005 | Erickson |
| 2005/0203599 | A1 | 9/2005 | Garabedian et al. |

FOREIGN PATENT DOCUMENTS

| EP | 0590431 A1 | 4/1994 |
| EP | 1048317 A1 | 11/2000 |
| WO | 0176495 A | 10/2001 |

*Primary Examiner*—Carl H Layno
*Assistant Examiner*—Yun Haeng Lee
(74) *Attorney, Agent, or Firm*—Fredrikson & Byron, P.A.

(57) ABSTRACT

A medical system for electrical stimulation includes a first column of electrodes, a second column of electrodes, an expandable member disposed between first and second columns, and an expansion mechanism adapted to transmit an externally applied pressure to the expandable member. The pressure expands the expandable member in order to force the first column of electrodes apart from the second column of electrodes. The first and second columns, disposed side-by-side, may be inserted through a percutaneous needle and into a epidural space, alongside a spinal cord; after insertion, the first column may be forced apart from the second column by applying the pressure to the expandable member.

45 Claims, 11 Drawing Sheets

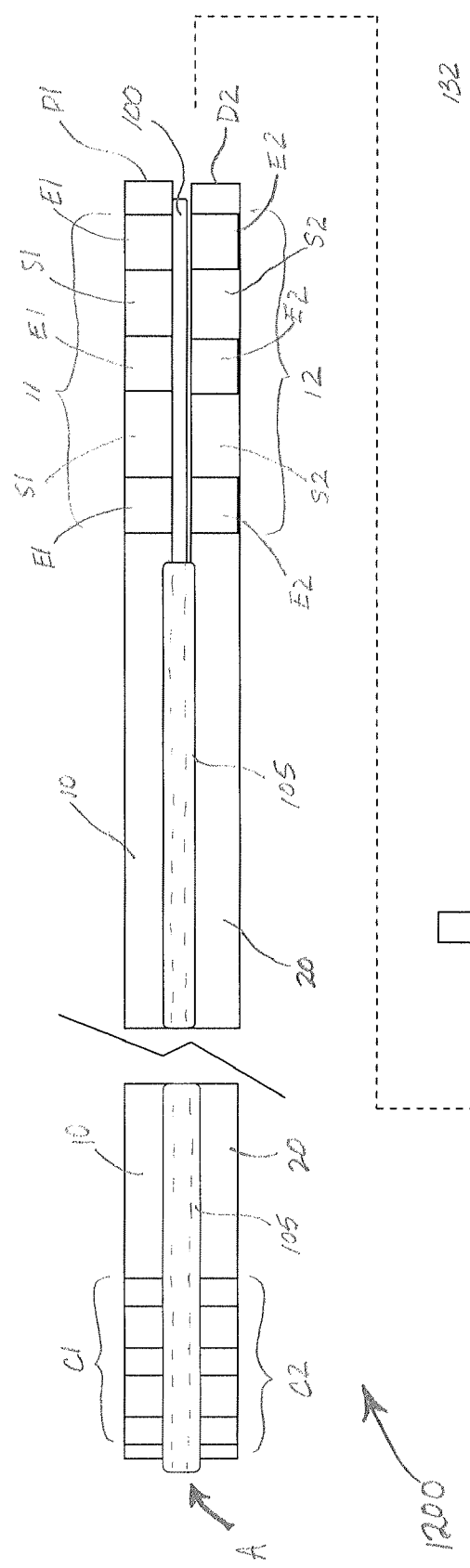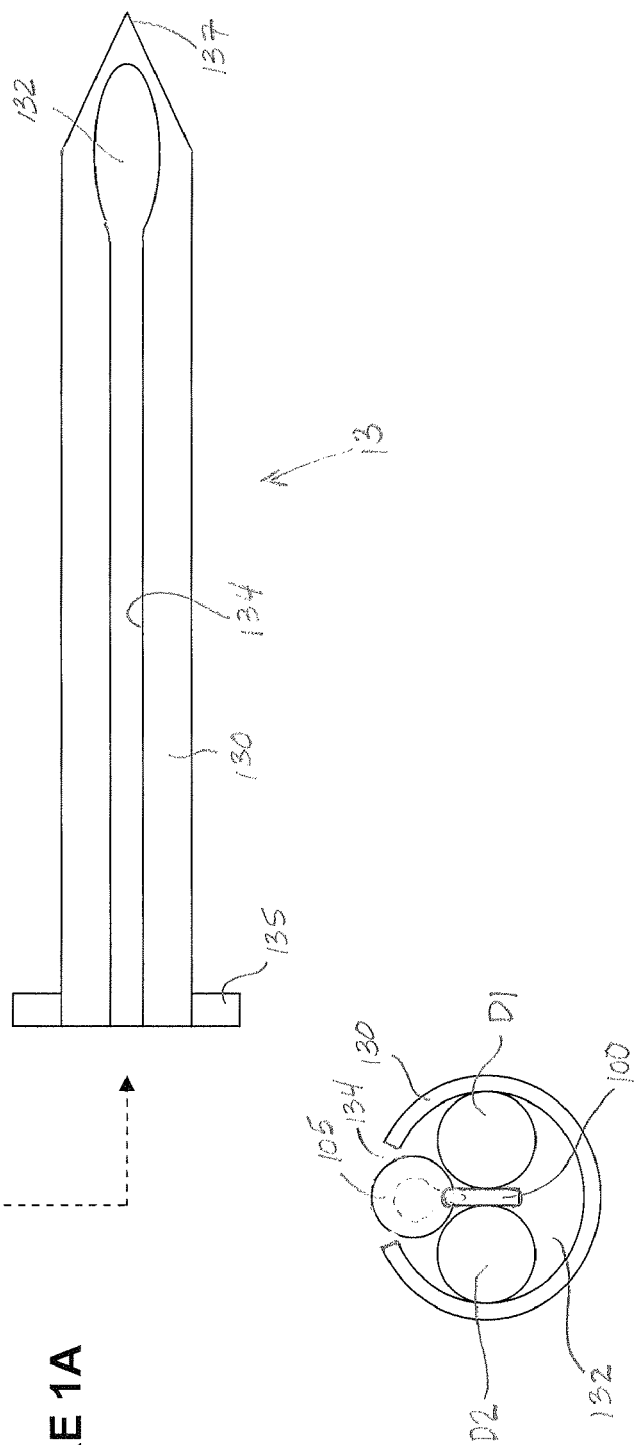
FIGURE 1A
FIGURE 1B

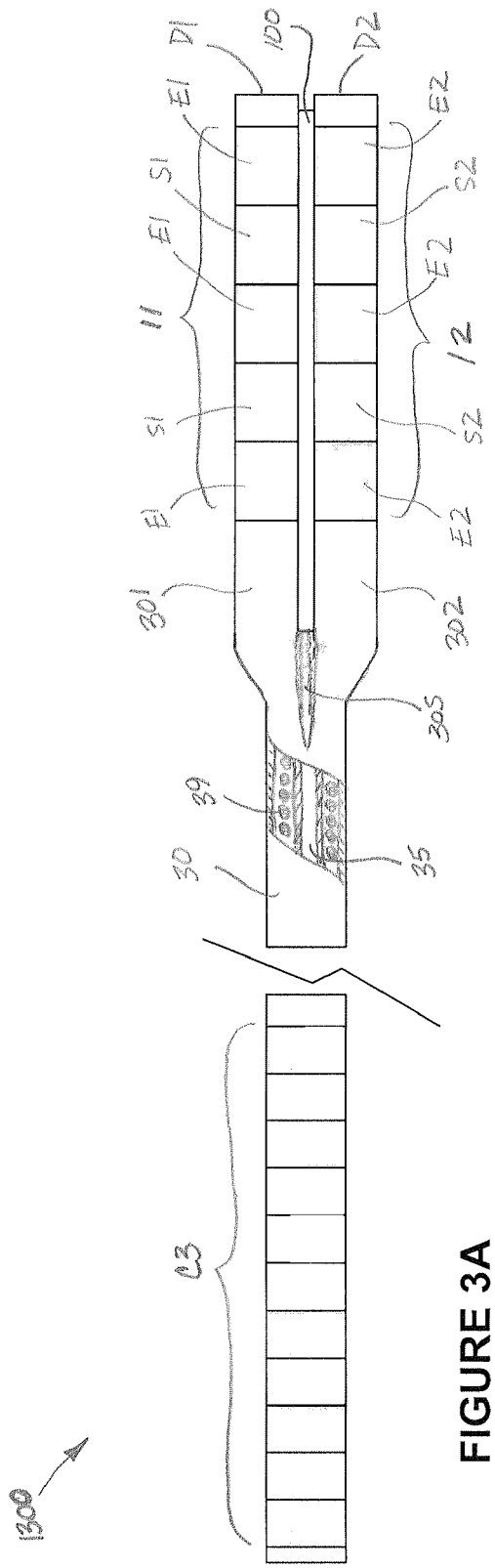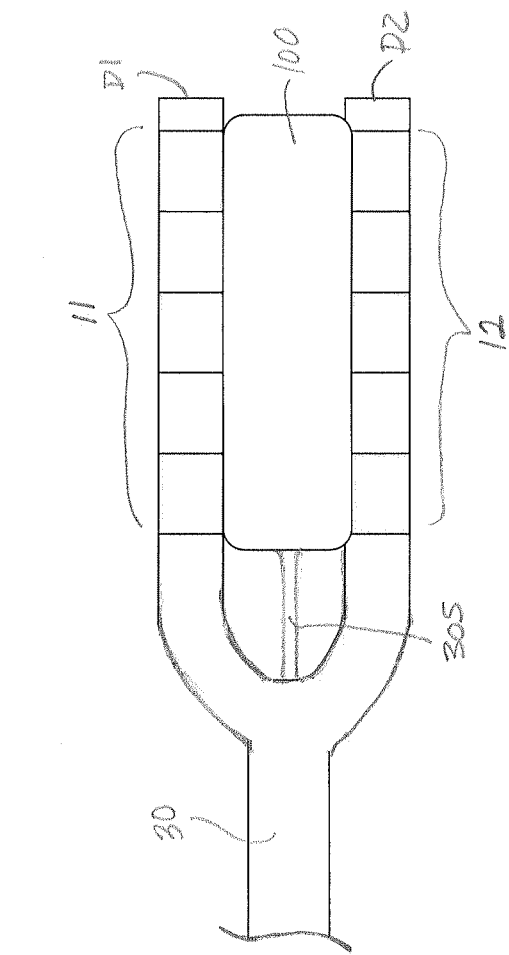
FIGURE 3A
FIGURE 3B
FIGURE 3C

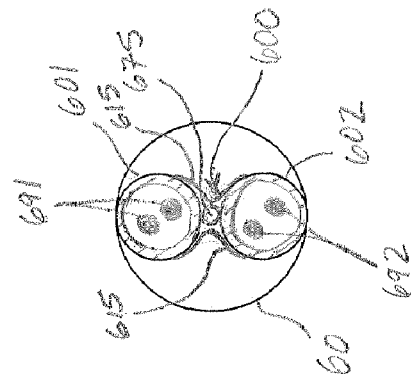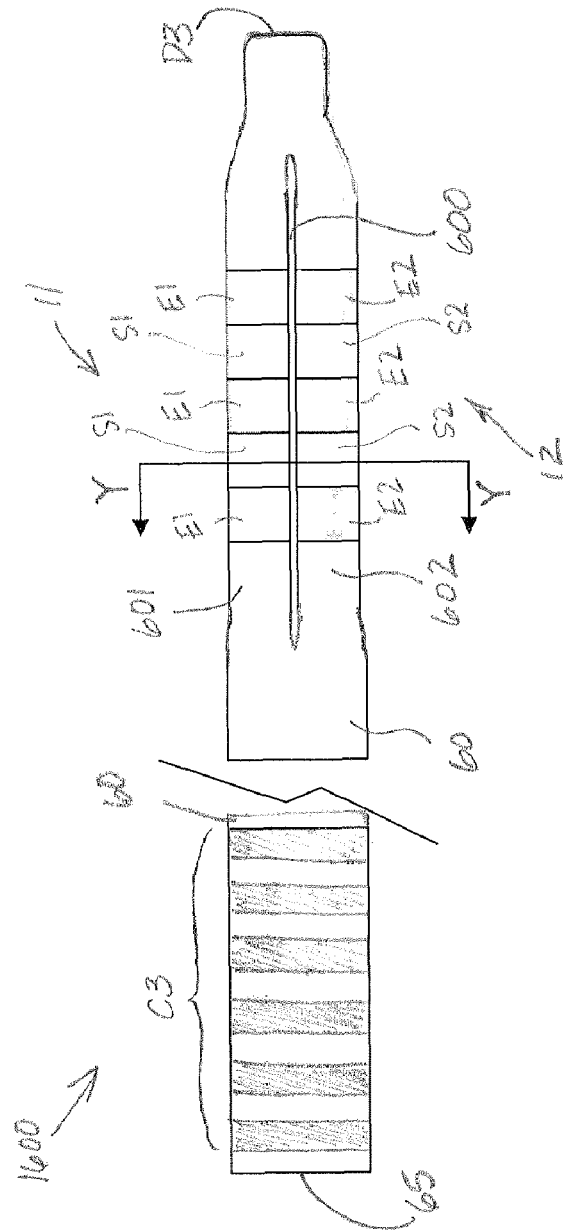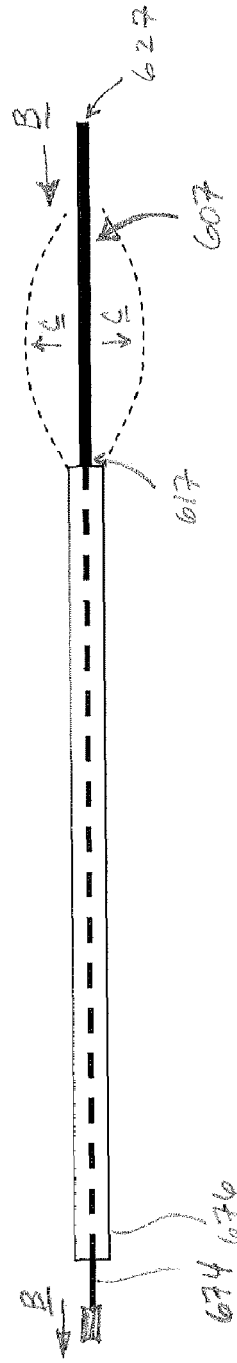
FIGURE 6B
FIGURE 6A
FIGURE 6C

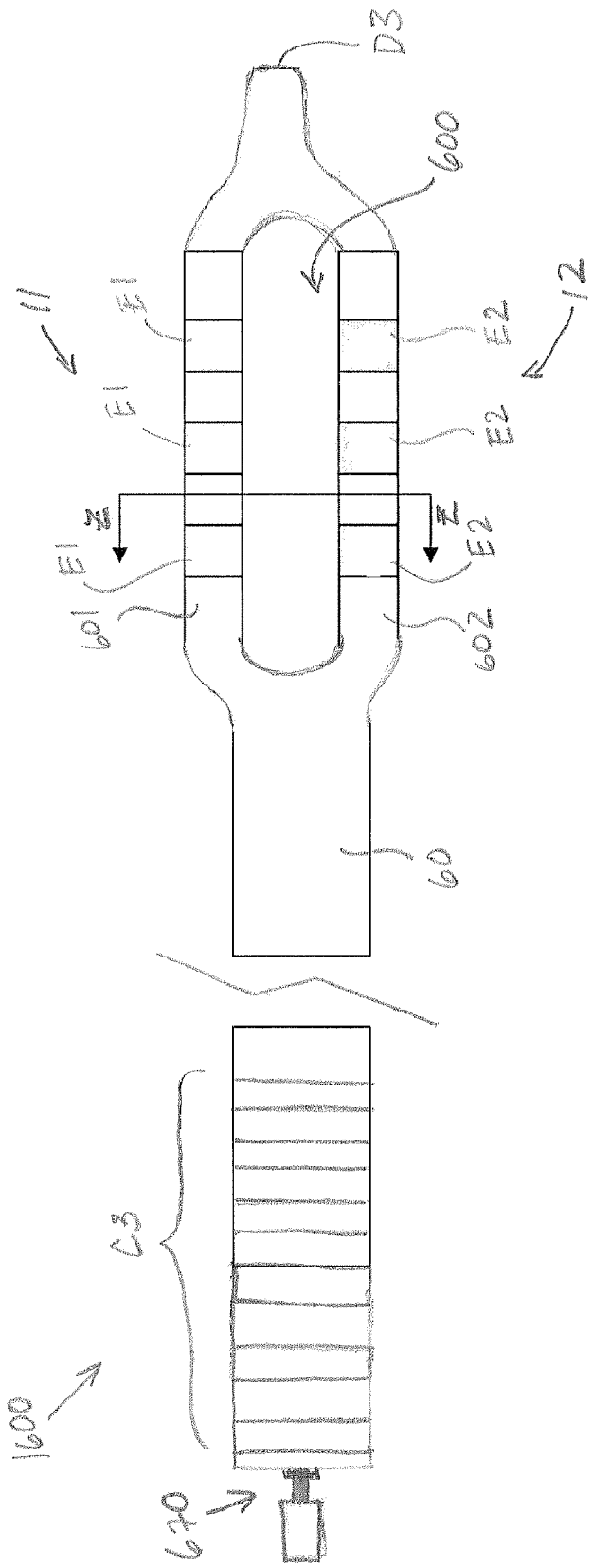
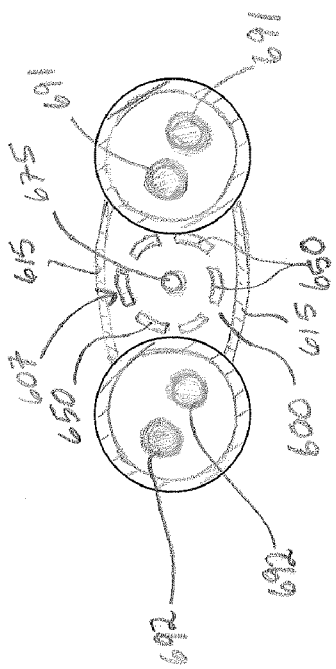
FIGURE 6D
FIGURE 6E

EXPANDABLE SYSTEMS FOR MEDICAL ELECTRICAL STIMULATION

TECHNICAL FIELD

The present invention pertains to systems for medical electrical stimulation and more particularly to stimulation systems that include a expandable member.

BACKGROUND

Medical electrical stimulation systems typically include one or more conductors that extend within an elongate insulative lead body and are coupled to one or more electrodes supported by the body. The one or more electrodes are typically coupled to a distal portion of the lead body so that, when the distal portion is implanted in a patient's body, the one or more electrodes are positioned to provide electrical stimulation therapy, for example, pain-relieving spinal stimulation from electrodes implanted along a spinal cord within an epidural space.

One type of spinal cord stimulation system includes a single column of electrodes, which is coupled along a distal portion of a lead body and has a profile that facilitates percutaneous delivery through a needle to an implant site along the spinal cord within the epidural space. Another type of spinal cord stimulation system includes at least two columns of electrodes coupled to a distal portion of a lead body; the at least two columns are spaced apart from one another so that a profile of the distal portion is often paddle-like and requires surgical implantation, because the size of the distal portion is too large to fit through a needle for percutaneous delivery. These paddle-type electrode assemblies, having more than one column of electrodes, provide flexibility for selection from a variety of stimulation patterns upon implantation without having to physically reposition the assemblies within the epidural space.

Some spinal cord stimulation systems, which include more than one column of electrodes and which collapse into a smaller profile for percutaneous implantation, are known in the art. Yet, there is still a need for spinal cord stimulation systems that include more than one column of electrodes and are designed to further facilitate operator control over the systems during an implant procedure thereby increasing an ease of implanting the electrode columns at desired locations.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIG. 1A is a plan view of a stimulation system and a percutaneous delivery needle, according to some embodiments of the present invention.

FIG. 1B is an end view of the system shown in FIG. 1A disposed within the needle.

FIG. 3A is a plan view of a stimulation system, according to some additional embodiments of the present invention.

FIG. 3B is an end view of the system of FIG. 3A disposed within a needle, according to some embodiments of the present invention.

FIG. 3C is a plan view of a distal portion of the system of FIG. 3A in an expanded condition.

FIG. 6A is a plan view of a stimulation system, according to further additional embodiments of the present invention.

FIG. 6B is a section view through section line Y-Y of FIG. 6A, according to some embodiments.

FIG. 6C is a plan view of an expansion element, according to some embodiments of the present invention.

FIG. 6D is another plan view of the system of FIG. 6A, wherein a distal portion thereof is expanded, according to some embodiments of the present invention.

FIG. 6E is a section view through section line Z-Z of FIG. 6D, according to some embodiments.

DETAILED DESCRIPTION

Figure 1C:
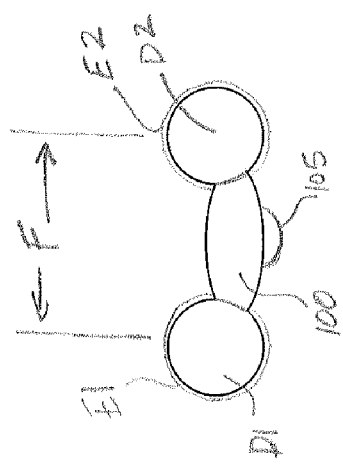
FIGS. 1C-D are an end view and a plan view, respectively, of a distal portion of the system of FIG. 1A in an expanded state or condition.

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

FIG. 1A is a plan view of a stimulation system 1200 and a percutaneous delivery needle 13, according to some embodiments of the present invention. FIG. 1A shows system 1200 configured for insertion into needle 13 (according to the dashed line arrow) for percutaneous implantation, for example, in an epidural space along a spinal cord, according to general implantation techniques which are known to those skilled in the art. FIG. 1A illustrates system 1200 including a first lead body 10 and a second lead body 20, wherein each body 10, 20 extends from a corresponding proximal connector assembly C1, C2 to a corresponding distal column of electrodes 11, 12; electrodes E1 of column 11 are separated from one another by insulative spacers S1, and each electrode E1 is coupled by a lead, or elongate conductor (not shown), which extends within body 10, to a corresponding connector contact of connector assembly C1; likewise electrodes E2 of column 12 are separated from one another by insulative spacers S2, and each electrode E2 of column 12 is coupled by a lead (not shown), which extends within body 20, to a corresponding connector contact of connector assembly C2. Those skilled in the art will appreciate that connector assemblies C1, C2 (and C3, introduced below) are adapted for coupling with a pulse generator, which is the electrical stimulation source for electrodes, and is typically implanted within a subcutaneous space apart from the stimulation site.

According to an exemplary embodiment, a length of spacers S1, S2 is between approximately 0.06 inch and approximately 0.24 inch, and a length of electrodes E1, E2 is approximately 0.12 inch. Column of electrodes 11 is shown disposed in proximity to a distal tip D1 of lead body 10, and column of electrodes 12 is shown disposed in proximity to a distal tip D2 of lead body 20. Although columns of electrodes 11, 12 are shown aligned with one another, so that each electrode E1 is adjacent a corresponding electrode E2, the scope of the invention is not so limited, and, according to other embodiments, one of columns 11, 12 is shifted proximally or distally so that electrodes E1 are not aligned with electrodes E2 as shown. Furthermore, a number of electrodes E1, E2 in each column 11, 12 is not limited to that illustrated herein, and may range from two to eight, or even more, for some embodiments.

FIG. 1A further illustrates system 1200 including an elongate tube or sidewall 105, through which a lumen (shown with dashed lines) extends, and an expandable member 100, shown in a collapsed, or unexpanded, state, disposed between columns of electrodes 11, 12. According to the illustrated embodiment, the lumen that extends within sidewall 105 provides a passageway for transmission of externally applied pressure to expandable member 100 in order to expand expandable member 100 to force apart columns 11, 12, after columns of electrodes 11, 12 have been passed through needle 13 and positioned against the spinal cord. Arrow A indicates a proximal opening of the lumen which provides access for an expansion mechanism to deliver the externally applied pressure through the lumen. It may be appreciated that an initial position of columns of electrodes 11, 12, achieved by passing the columns out from the needle, may be adjusted prior to delivering the externally applied pressure to expandable member 100. According to some preferred embodiments, the expansion mechanism comprises an inflation medium, which may be delivered via a syringe-type tool to inflate expandable member 100. Although expansion member 100 is preferably coupled to each lead body 10, 20, for example, either all along columns of electrodes 11, 12, or to one or all of spacers S1, S2, or just proximal to columns 11, 12 and/or just distal to columns 11, 12, sidewall 105 is, preferably, not coupled to lead bodies 10, 20, since sidewall 105 is preferably rigid and will not expand when columns 11, 12 are forced apart by expandable member 100.

FIG. 1A further illustrates needle 13 including a sidewall 130 extending about a lumen 132 and longitudinally between a piercing distal tip 137 and a proximal hub 135; sidewall 130 includes a slot 134 extending along a length thereof. FIG. 1B is an end view of system 1200 disposed within needle 13, for example, for percutaneous implantation. FIG. 1B illustrates a fit of collapsed system 1200 within a lumen 132 of needle 13 wherein sidewall 105 protrudes into slot 134. With reference to FIG. 1B, it will be appreciated that expansion element 100, being in a collapsed state, allows both lead bodies 10, 20 to fit side-by-side within needle lumen 132. According to some alternate embodiments, sidewall 105 may be collapsible so that a needle lumen without a sidewall slot, such as slot 134, can accommodate both lead bodies 10, 20 and sidewall 105.

Figure 1D:
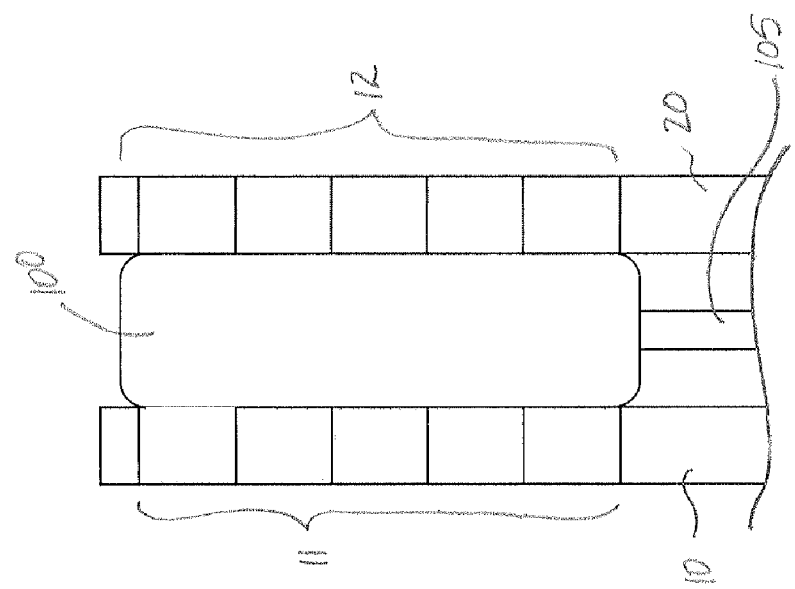

According to some methods of the present invention, once needle 13, via piercing tip 137, has been inserted into an epidural space, distal tips D1, D2 of bodies 10, 20 are inserted into needle lumen 132, and bodies 10, 20 are pushed through lumen 132 to advance columns of electrodes 11, 12 into the epidural space; after columns 11, 12 have been pushed out from needle 13, and positioned at target implant site along the spinal cord, a pressure is applied to expandable member 100 causing member 100 to expand and force columns 11, 12, apart from one another for example, as illustrated in FIGS. 1C-D. Expandable member 100 may be inflated, as previously described, to force columns 11, 12 apart, or member 100 may be comprised of a cellular sponge-like material that swells when a fluid is injected though the lumen of sidewall 105; additional embodiments of expandable members will be described below.

FIGS. 1C-D are an end view and a plan view, respectively, of the system of FIG. 1A in an expanded state or condition. FIGS. 1C-D illustrate expandable member 100 having been expanded to force columns of electrodes 11, 12 into a position in which the columns are spaced apart from one another by a distance F; columns 11, 12 are preferably approximately parallel to one another in the illustrated position. Distance F may range from approximately 1.5 mm to approximately 4 mm, and, according to some embodiments of the present invention, expandable member 100, or any of the other embodiments of expandable members described herein, may be expanded to different degrees for multiple separations, or distances F, between columns of electrodes 11, 12 in order to provide a flexibility, at the time of implant, in spacing columns 11, 12 apart at a distance which is most suitable for stimulation therapy.

Figure 2:
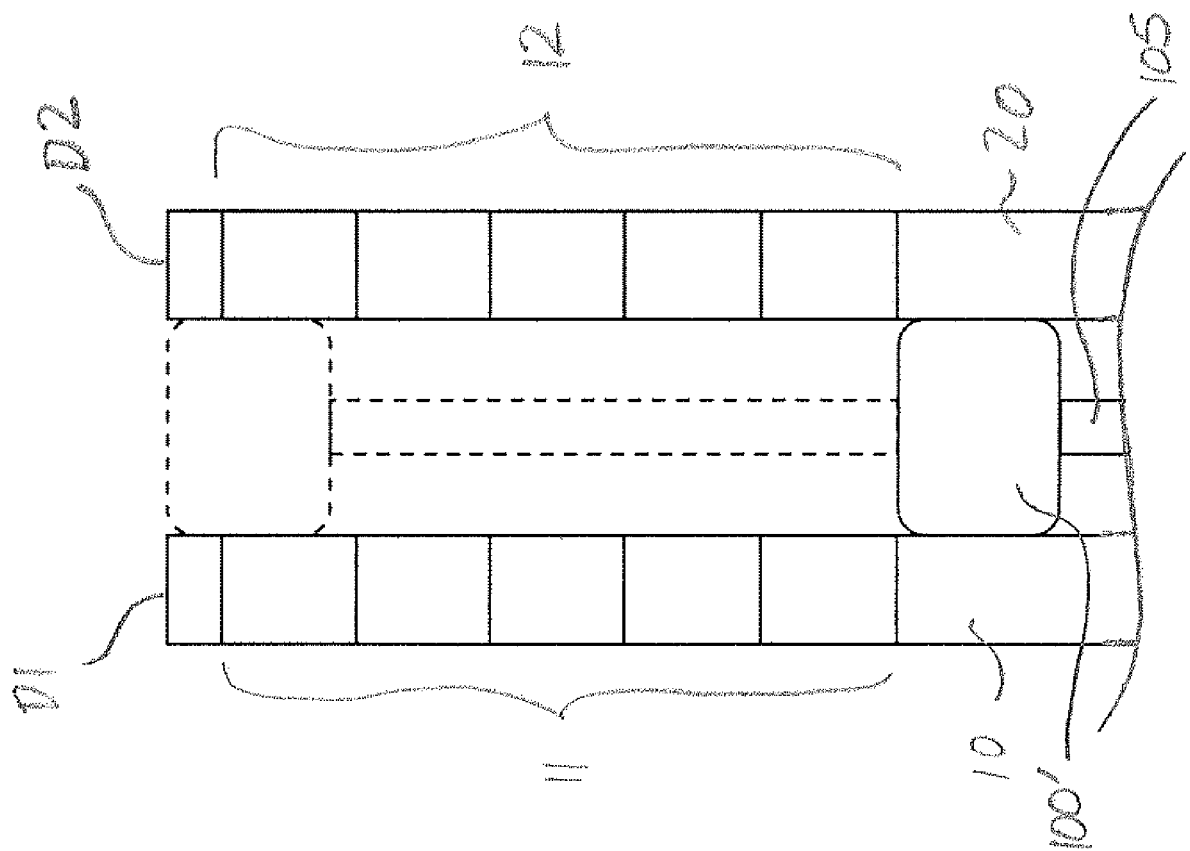
FIG. 2 is a plan view of an expanded distal portion, according to some alternate embodiments of the present invention.

FIG. 1D further illustrates expandable member 100 extending alongside and over a length of columns of electrodes 11, 12, however, expandable member can vary in location and extent with respect to columns 11, 12 to form alternate embodiments. FIG. 2 is a plan view of an expanded distal lead portion, according to some such alternate embodiments. FIG. 2 illustrates an expandable member 100' disposed just proximal to columns of electrodes 11, 12, and, with dashed lines, an alternate or additional location for member 100'. According to the illustrated embodiment, columns 11, 12 have sufficient stiffness to be displaced by the relatively limited extent illustrated for member 100'.

FIG. 3A is a plan view of a stimulation system 1300, according to some additional embodiments of the present invention. FIG. 3A illustrates system 1300 including a lead body 30 extending distally from a connector assembly C3 to a bifurcation from which first and second distal lead bodies 301, 302 extend; first column of electrodes 11 is coupled to first distal lead body 301 and second column of electrodes 12 is coupled to second distal lead body 302. Each electrode E1 of column 301 and each electrode E2 of column 302 is coupled to a corresponding connector contact of connector assembly C3, for example, by a corresponding filar of a multi-conductor coil 39, each filar of coil 39 being a conductive wire, for example MP35N wire, isolated from the others via a coating of electrical insulation, for example, comprised of polyimide, PTFE, and/or ETFE. FIG. 3A further illustrates a lumen 35 extending within body 30 and being surrounded by a sidewall 305 just proximal to expandable member 100; a proximal opening of lumen 35 is preferably located in proximity to connector assembly C2 for the introduction of an expansion mechanism.

FIG. 3B is an end view of system 1300 assembled within a needle 13' for a percutaneous implantation; a plan view of needle 13' would be similar to that of needle 13 as shown in FIG. 1A, with the exception of the absence of a slot in a sidewall 130' of needle 13'. As previously described for system 1200, distal ends D1, D2 may be inserted through needle 13', which has been inserted into the epidural space, and body 30 pushed to pass columns of electrodes 11, 12 out from needle 13' into the epidural space alongside the spinal cord. After columns 11, 12 have been positioned at a target stimulation site, expandable member 100 may be expanded by the expansion mechanism, for example, a pressurized inflation fluid introduced through lumen 35, in order to force columns 11, 12 apart, for example, as illustrated in FIG. 3C. FIG. 3C is a plan view showing first and second columns 11, 12 spaced apart from one another by expanded member 100 and, preferably, approximately parallel with one another. As previously described for system 1200, expandable member 100 may be expanded to different degrees for multiple separations between columns of electrodes 11, 12 in order to provide a flexibility, at the time of implant, in spacing columns 11, 12 apart at a distance that is most suitable for stimulation therapy.

Figure 4:
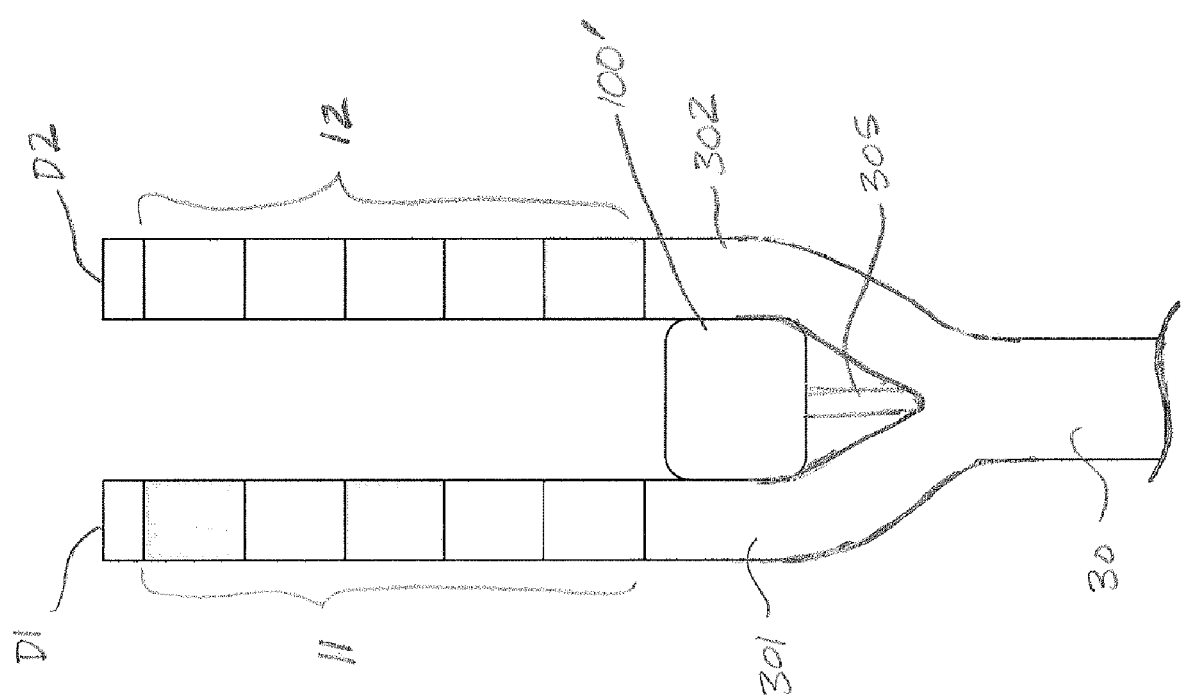
FIG. 4 is a plan view of an expanded distal portion, according to an alternate embodiment of the present invention.

FIG. 3C further illustrates expandable member 100 extending alongside and over a length of columns of electrodes 11, 12, but, according to alternate embodiments, expandable member varies in location and extent with respect to columns 11, 12. FIG. 4 is a plan view of an expanded distal lead portion, according to some such alternate embodiments. Similar to FIG. 2, FIG. 4 illustrates expandable member 100' disposed just proximal to columns of electrodes 11, 12. According to the illustrated embodiment, columns 11, 12 have sufficient stiffness to be displaced by the relatively limited extent illustrated for member 100'. Although sidewall 305 through which lumen 35 extends is shown, in both FIG. 3C and FIG. 4, as extending beyond the bifurcation of body 30, alternate embodiments of the present invention include an expandable member extending proximally to an opening of lumen 35 in bifurcation, such that lumen 35 need not extend distally beyond bifurcation.

Figure 5A:
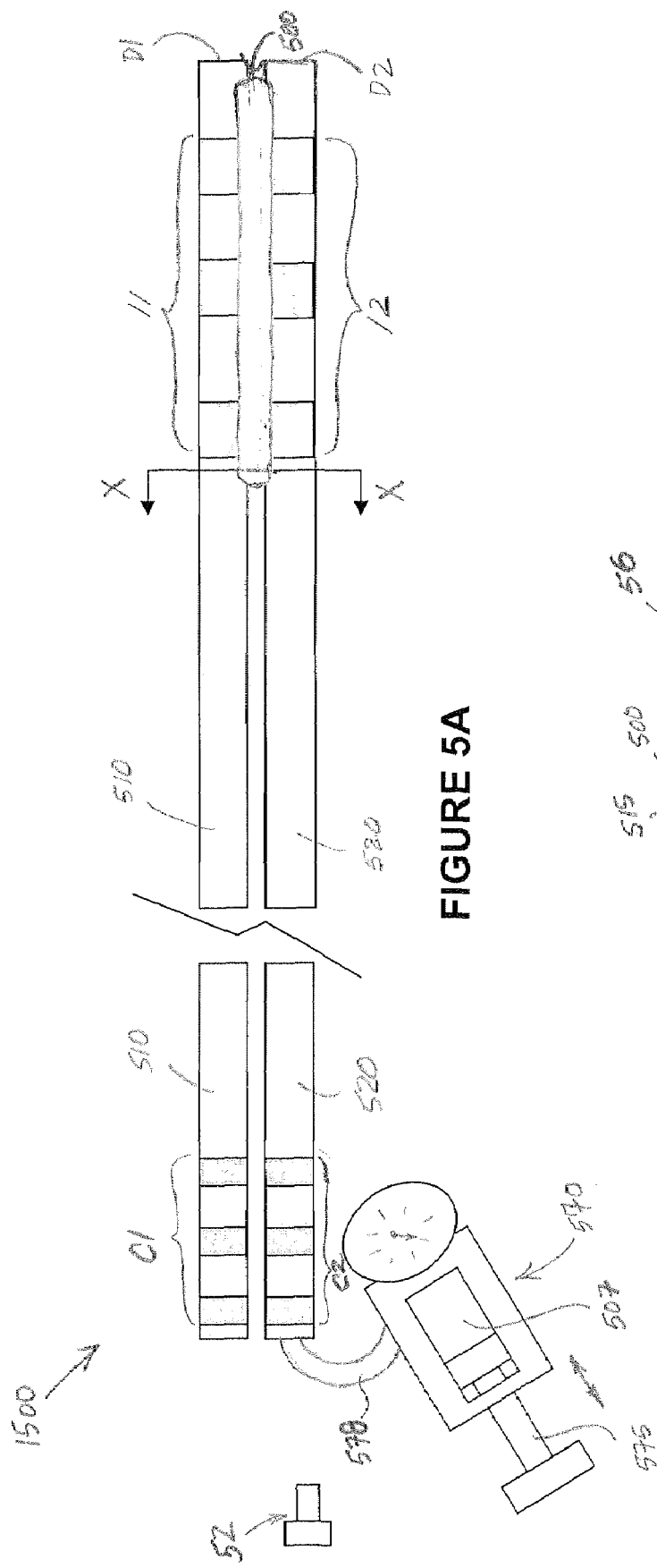
FIG. 5A is a plan view of a stimulation system, according to some additional embodiments of the present invention.
Figure 5B:
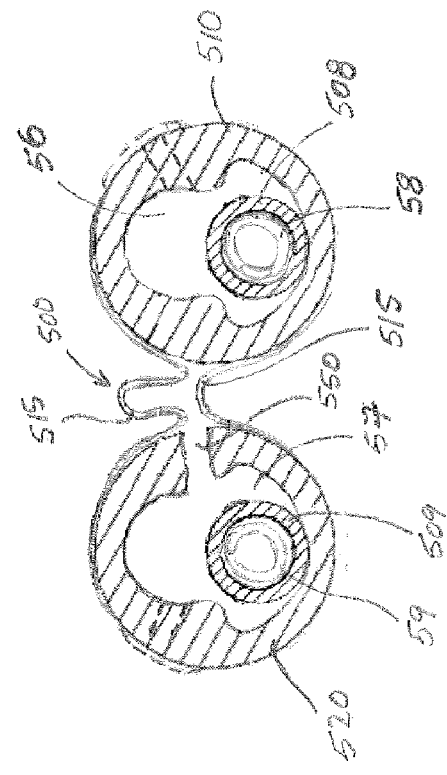
FIG. 5B is a section view through section line X-X of FIG. 5A, according to some embodiments.

FIG. 5A is a plan view of a stimulation system 1500, according to some additional embodiments of the present invention; and FIG. 5B is a section view through section line X-X of FIG. 5A, according to some embodiments. FIGS. 5A-B illustrate system 1500 including a first lead body 510 and a second lead body 520, wherein each body 510, 520 extends from a corresponding proximal connector assembly C1, C2 to the corresponding distal column of electrodes 11, 12; each electrode E1 of column 11 is coupled by a corresponding filar of a multi-conductor coil 58 to a corresponding connector contact of connector assembly C1; likewise, each electrode E2 of column 12 is coupled by a corresponding filar of a multi-conductor coil 59 to a corresponding connector contact of connector assembly C2. (Filars of coils 58, 59 may be similar in construction to those described above for coil 39.) FIG. 5B shows each body 510, 520 including a lumen 56, 57, respectively, and optional inner sheaths 508, 509 extending around respective coils 58, 59 and within respective lumens 56, 57.

FIGS. 5A-B further illustrate an expandable member 500 disposed between columns of electrodes 11, 12 and formed by walls 515 which are coupled to bodies 510, 520, for example, via adhesive and/or thermal bonding, and an inflation device 570 coupled to a proximal end of body 520; a tubular member 578 of inflation device 570 is in fluid communication with lumen 57. According to the illustrated embodiment, inflation device 570 includes a chamber 507 holding an inflation medium, or fluid, which acts as an expansion mechanism for transmitting a pressure applied by a plunger 575 of inflation device 570; the inflation fluid, being transmitted, through lumen 57 and into expandable member 500, via a port 550 of lumen 57, and pressurized by plunger 575, inflates expandable member 500 by spreading walls 515, for example as illustrated in FIG. 5C. After member 500 has been inflated, device 570 may be detached from lumen 57 and replaced with a plug 52 to seal off the proximal end of lumen 57 in order to maintain inflation pressure within member 500. However, it should be noted that, according to alternate embodiments, it is not necessary to hold the inflation pressure within member 500 in order to maintain a desired separation between columns 11, 12, after the initial inflation.

According to preferred embodiments of the present invention, walls 515 of expandable member 500 are relatively thin, for example, ranging from approximately 0.0002 inch to approximately 0.004 inch, and are formed from a relatively compliant material, for example, silicone, low to medium durometer urethane, or polyolefin copolymer (POC); according to other embodiments, walls 515 are formed from a relatively non-compliant material, for example, polyethylene terephthalate (PET). In some embodiments of the present invention, expandable member 500 may initially be formed, according to methods known to those skilled in the art, as a balloon whose outer surface may subsequently be bonded to bodies 510, 520.

Figure 5D:
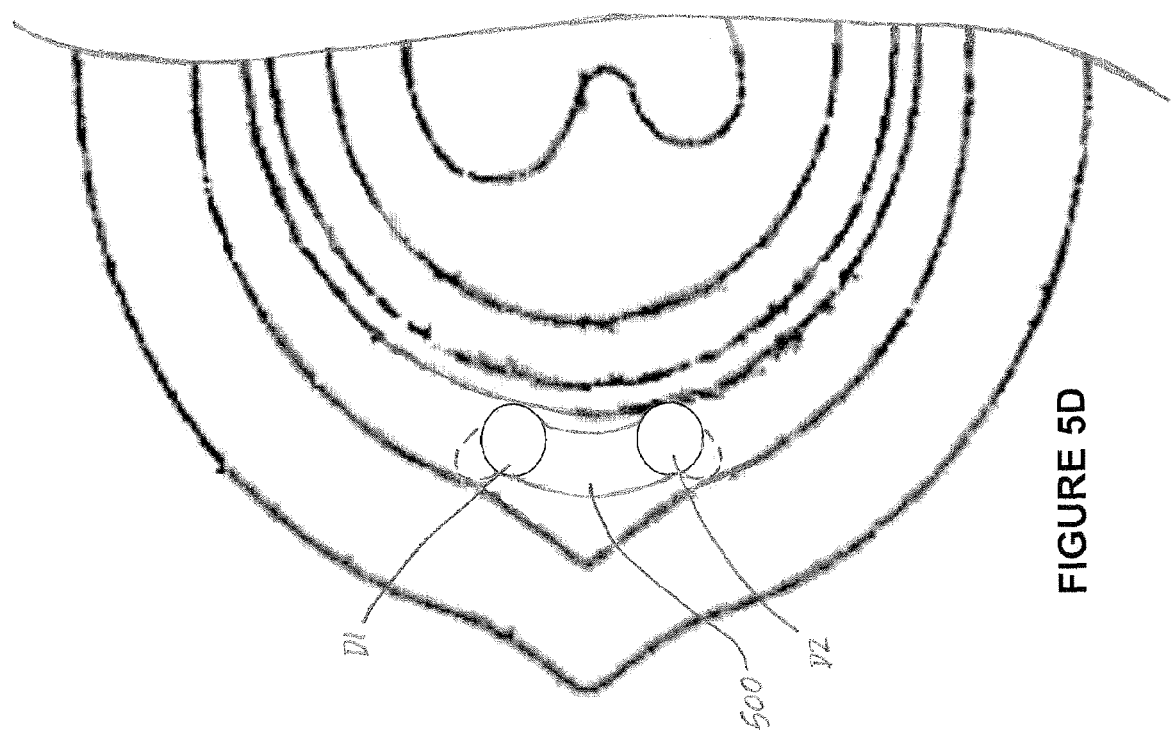
FIG. 5D is a schematic end view of the distal portion of FIG. 5C implanted along a spinal cord in an epidural space.
Figure 5C:
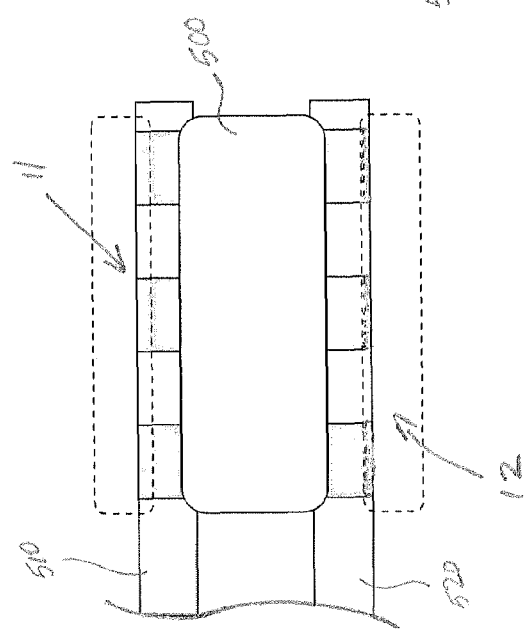
FIG. 5C is a plan view of an expanded distal portion of the system shown in FIG. 5A.

FIG. 5C is a plan view of the expanded distal lead portion of system 1500; and FIG. 5D is a schematic end view of the expanded distal lead portion implanted along a spinal cord in an epidural space. With reference to FIGS. 5C-D, it may be appreciated that expanded member 500 forces columns of electrodes 11, 12 to be spaced apart from one another, for example, in a configuration mimicking that of a paddle-type surgical lead, and that a flexibility of expanded member 500 facilitates conformance within the epidural space, such that electrodes E1, E2 of columns 11, 12 make good contact with the dura mater enclosing the spinal cord. FIGS. 5B-D further illustrate with dashed lines additional expandable members and corresponding ports (FIG. 5B) extending from corresponding lumens 56, 57 for inflation thereof; according to some embodiments of the present invention, these additional members may be added to enlarge the distal lead portion of system 1500, for a snug fit within the epidural space. Alternately, expandable member 500 may expand to a larger size for the snug fit, without compromising electrode contact with the dura mater, for example as illustrated in FIG. 5E, which is another schematic end view of the expanded distal lead portion implanted in the epidural space.

Figure 5E:
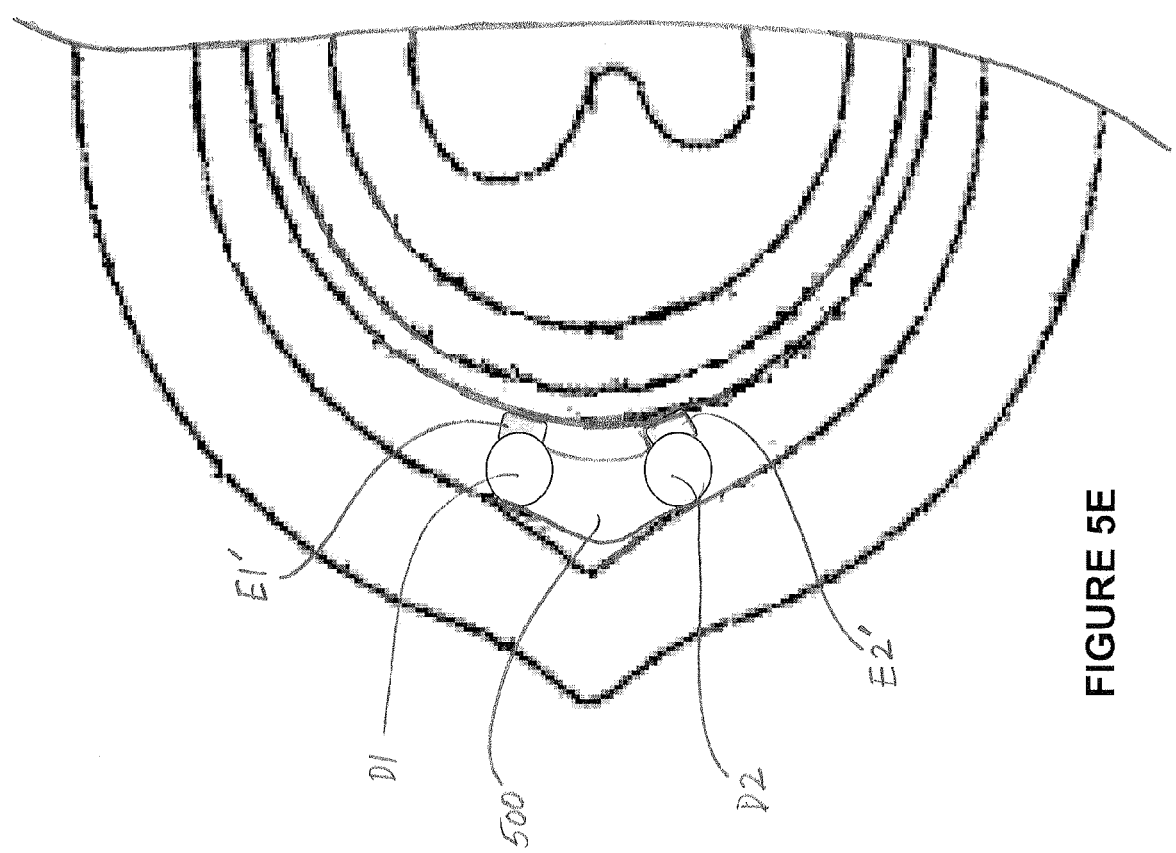
FIG. 5E is a schematic end view of an expanded distal portion implanted in the epidural space and having electrodes configured according to some alternate embodiments of the present invention.

Electrodes E1, E2 have heretofore been illustrated as rings extending about respective lead bodies, but FIG. 5E illustrates an alternate embodiment: electrodes E1', E2', which each have a relatively flat surface for stimulating contact. Each electrode E1', E2' may be formed, for example, as a plate mounted on the respective lead bodies 510, 512, being either coupled directly with the corresponding conductive filar of respective coil 58, 59 (FIG. 5B), or coupled to a conductive ring, which is, in turn coupled to the corresponding conductive filar; an example of the latter construction is described for a surgical-type lead in co-pending and commonly assigned patent application Ser. No. 11/413,582, salient portions of which are hereby incorporated by reference. According to other contemplated embodiments, columns of electrodes 11, 12 are incorporated into an expandable element, for example, element 100 or 500, wherein the electrodes are coupled to a surface of the expandable element; such electrodes may be rigid or formed from a flexible material, for example, from a foil.

FIG. 6A is a plan view of a stimulation system 1600, according to further additional embodiments of the present invention; and FIG. 6B is a section view through section line Y-Y of FIG. 6A, according to some embodiments. FIGS. 6A-B illustrate system 1600 including a lead body 60 extending distally from connector assembly C3 to a bifurcation from which a first distal lead body 601, to which column of electrodes 11 is coupled, and a second distal lead body 602, to which column of electrodes 12 is coupled, each extend; each electrode E1 of column 11 is coupled by a corresponding conductor 691 to a corresponding connector contact of connector assembly C3, and each electrode E2 of column 12 is coupled by a corresponding conductor 692 to a corresponding connector contact of connector assembly C3. FIG. 6A further illustrates a single distal tip D3 terminating distal bodies 601, 602. According to the illustrated embodiment, a lumen 675 extends through lead body 60 from a proximal opening 65, in proximity to connector assembly C3, to a distal opening at the bifurcation, the distal opening providing fluid communication between lumen 675 and an expandable area 600, which is enclosed by sidewalls 615.

FIG. 6C is a plan view of an expansion element 670, according to some embodiments of the present invention, which is adapted for insertion into expandable area 600, via lumen 675. FIG. 6C illustrates expansion element 670 including a first elongate member 674 extending within a second elongate member 676, and an expandable member 607. FIG. 6C further illustrates a distal end of second elongate member 676 coupled to a proximal end 617 of expandable member 607, and a distal end of first elongate member 674 coupled to a distal end 627 of expandable member 607, so that elongate member 674 forms an expansion mechanism for expandable member 607. According to the illustrated embodiment, when first elongate member 674 is pulled in a direction corresponding to arrow B, distal end 627 of expandable member 607 is brought closer to proximal end 617 thereby expanding expandable member 607 per arrows C, for example, as illustrated with dashed lines in FIG. 6C, and as illustrated, for some embodiments, in FIG. 6E.

FIG. 6D is another plan view of system 1600, according to some embodiments of the present invention, wherein a distal portion thereof is expanded by insertion and subsequent expansion of expansion element 670 within walls 615 of expandable area 600. FIG. 6E is a section view through section line Z-Z of FIG. 6D, according to some embodiments, wherein expandable member 607 is formed by a plurality of flexible slats 650, which are coupled together at proximal and distal ends 617, 627, and thus bent outward when first elongate member 674 pulls distal end 627 toward proximal end 617. According to the illustrated embodiment, after system 1600, in an unexpanded state (FIG. 6A), has been inserted into the epidural space alongside the spinal cord, for example, via a percutaneous needle, expansion element 670 may be inserted into proximal opening 65 of lumen 675 and advanced therein until expandable element 607 resides in expandable area 600. (Alternately, element 670 may be inserted into area 600 prior to insertion of system 1600 into the epidural space.) When system 1600 is within the epidural space, and expandable element 607 resides within expandable area 600, first elongate member 674 of element 607 may be pulled with respect to second elongate element 676 to expand expandable member 607 thereby expanding expandable area 600 and forcing first column of electrodes 11 apart from second column of electrodes 12, for example, as illustrated in FIGS. 6D-E. According to preferred embodiments, after expansion element 670 has expanded expandable area 600, expandable member 607 of element 670 may be collapsed, by pushing first elongate member 674 back into the position shown in FIG. 6C, and element 670 withdrawn from system 1600 to leave the system in the expanded state, as is illustrated in FIG. 6D.

It should be noted that, although body 60 of system 1600 has been described to include lumen 675 for passage of expansion element, alternate embodiments of the present invention need not include such a lumen. According to some such alternate embodiments, an entry for passage of expansion mechanism 670 into expandable area 600 may be formed in body 60 in close proximity to bifurcation and expandable area 600, or through one of walls 615 of expandable area 600. According to some other alternate embodiments, a lumen for passage of expansion element 670 may be provided by a sidewall external to body 60, wherein the sidewall extends alongside body 60 to join with expandable area 600 being either attached to, or detached from body 60.

Figure 7A:
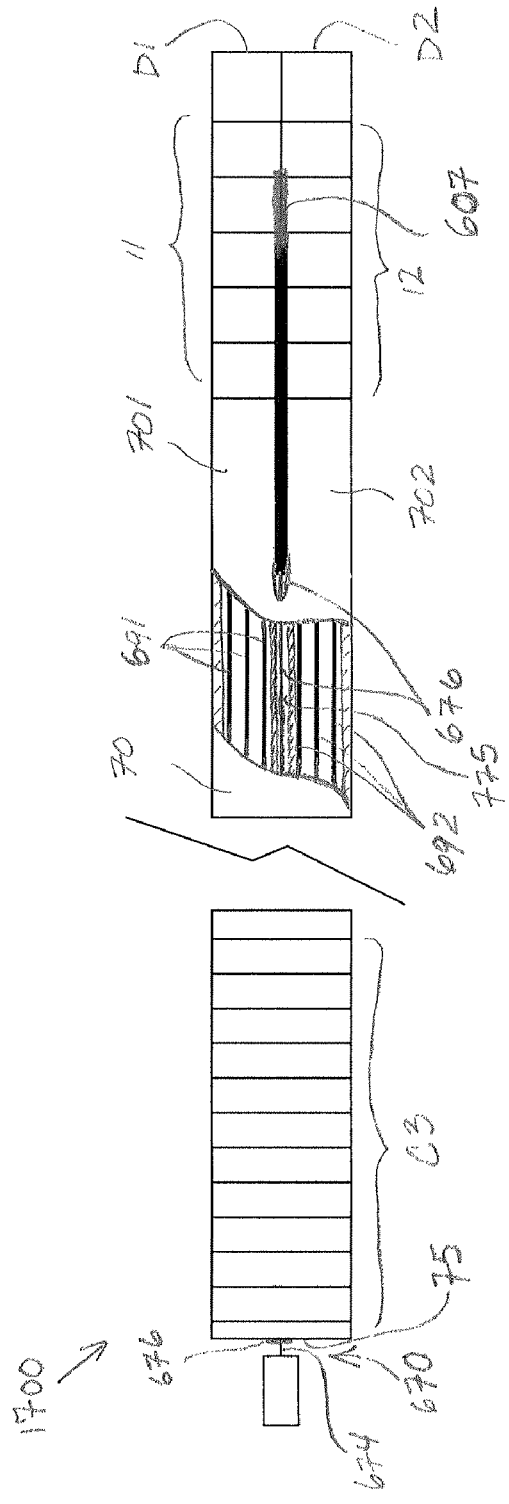
FIG. 7A is a plan view including a partial cut-away section of a stimulation system, according to yet further additional embodiments of the present invention.

FIG. 7A is a plan view including a partial cut-away section of a stimulation system 1700, according to yet further additional embodiments of the present invention. FIG. 7A illustrates system 1700 including a lead body 70 extending distally from connector assembly C3 to a bifurcation from which distal lead bodies 701, 702 extend to corresponding distal tips D1, D2; column of electrodes 11 is coupled to lead body 701 and column of electrodes 12 to lead body 702, wherein each of electrodes E1 is coupled to a corresponding connector contact of connector assembly C3 via the corresponding conductor 691, and each of electrodes E2 is coupled to a corresponding connector contact of connector assembly C3 via the corresponding conductor 692. FIG. 7A further illustrates expansion element 670 having been inserted into a proximal port 75 of a lumen 775 of body 70, and advanced within lumen 775 so that expandable member 607 has exited lumen 775 at a distal port 71. According to the illustrated embodiment, expandable member 607 is disposed in an area between electrode columns 11, 12, which is not enclosed by expandable walls, for example walls 615 of system 1600, and may be expanded, as previously described in conjunction with FIGS. 6C-E, to force columns of electrodes 11, 12 apart, for example, as is illustrated in FIG. 7B.

Figure 7B:
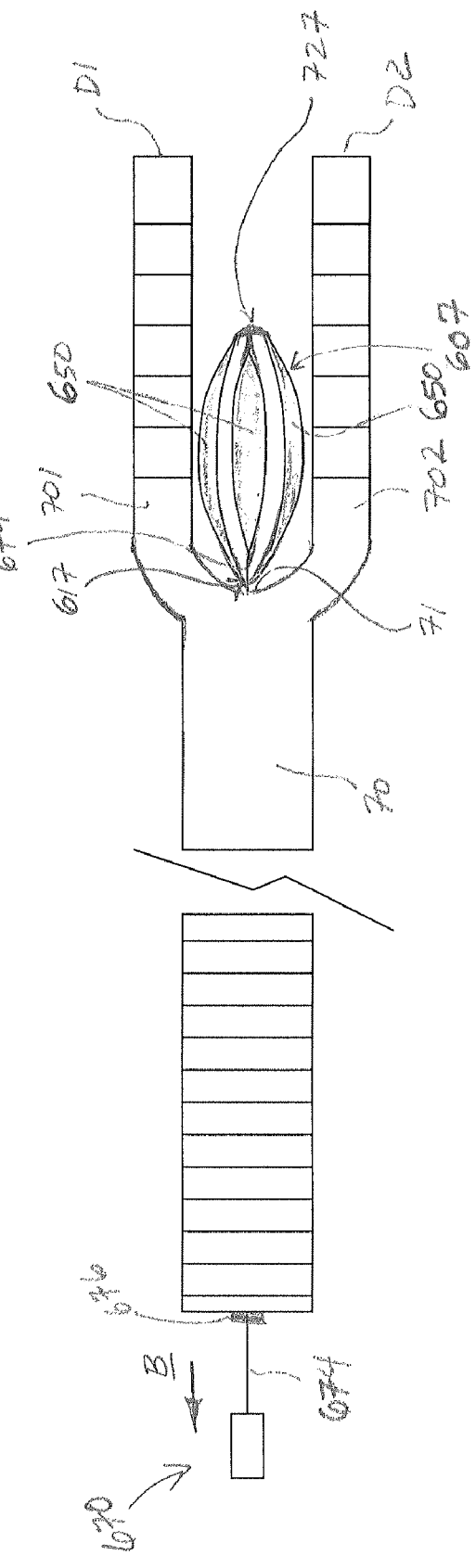
FIG. 7B is a plan view of the system shown in FIG. 7A wherein a distal portion thereof is expanded, according to some embodiments of the present invention.

FIG. 7B is a plan view of the system 1700 wherein a distal portion thereof is expanded, according to some embodiments of the present invention. FIG. 7B illustrates distal end 627 of expandable member 607 having been pulled, via first elongate member 674, per arrow B, to expand slats 650, thereby spacing apart columns of electrodes 11, 12. According to preferred embodiments, after columns of electrodes 11, 12 have been forced into the spaced apart position, expansion element 670 is collapsed and withdrawn through lumen 775.

It should be noted that an alternate embodiment of expansion element 670 includes a balloon, in place of slats 650, as expandable member 607, and second elongate member 676, rather than being disposed about first elongate member 674, is disposed about an inflation lumen. According to this embodiment, second elongate member 676 is adapted to couple with an inflation device, for example device 570 shown in FIG. 5A, that will apply a pressure via an inflation medium to expand member 607.

In the foregoing detailed description, the invention has been described with reference to specific embodiments. However, it may be appreciated that various modifications and changes can be made without departing from the scope of the invention as set forth in the appended claims. Furthermore, the embodiments of the invention described herein have been described in the context of spinal cord stimulation, yet those skilled in the art should appreciate that embodiments of the present invention may be applied in other contexts, for example, cardiac sensing and stimulation, either endocardial or epicardial.

We claim:

1. A medical system for electrical stimulation of a spinal cord, the system comprising:
   a first column of electrodes, and a second column of electrodes extending alongside the first column of electrodes, each of the first and second columns of electrodes including at least a first electrode separated from a second electrode by an insulative spacer, and each of the first and second columns of electrodes having a length that is defined from a proximal end of the respective first electrode to a distal end of the respective second electrode;
   an expandable member disposed between the first and second columns of electrodes; and
   an expansion mechanism adapted to transmit externally applied pressure to expand the expandable member, the expansion of the expandable member forcing each of the first column of electrodes and the second column of electrodes into a respective position in which the first and second columns of electrodes are spaced apart from one another and the length of the first column extends approximately parallel with the length of the second column;
   wherein the expandable member comprises a first expandable member, and further comprising:
   a second expandable member extending alongside the first column of electrodes and being offset from the first expandable member about a perimeter of the first column of electrodes; and
   a third expandable member extending alongside the second column of electrodes and being offset from the first expandable member about a perimeter of the second column of electrodes; and
   wherein the expansion mechanism is further adapted to transmit externally applied pressure to expand the second and third expandable members.

2. The system of claim 1, wherein:
   the first column of electrodes is coupled to a first body, the first body including a distal tip; and
   the second column of electrodes is coupled to a second body, the second body including a distal tip unattached to the first body distal tip, such that, when the first and second columns of electrodes are in the spaced apart position, the first body distal tip is spaced apart from the second body distal tip.

3. The system of claim 1, wherein the expandable member extends along an entirety of the length of each of the first and second columns of electrodes.

4. The system of claim 1, wherein the expandable member extends alongside at least a portion of the length of each of the first and second columns of electrodes.

5. The system of claim 1, wherein:
   the expandable member comprises an inflatable chamber; and
   the expansion mechanism comprises an inflation medium.

6. The system of claim 1, wherein:
   the expandable member includes a first end and a second end and extends between the first end and the second end; and
   the expansion mechanism comprises an elongate member adapted to bring the first end of the expandable member closer to the second end of the expandable member to expand the member.

7. The system of claim 1, further comprising a sidewall surrounding a lumen, the lumen extending proximally from the expandable member and providing a passageway for the transmission of externally applied pressure.

8. The system of claim 7, further comprising:
   a body extending proximally from one of the first and second columns of electrodes; and
   wherein the sidewall surrounding the lumen is a part of the body.

9. The system of claim 7, further comprising:
   a body extending proximally from one of the first and second columns of electrodes; and
   wherein the sidewall surrounding the lumen is separate from the body.

10. The system of claim 1, further comprising a body extending proximally from both the first and second columns of electrodes, the body including a lumen extending proximally from the expandable member and providing a passageway for the transmission of externally applied pressure.

11. A medical system for electrical stimulation of a spinal cord, the system comprising:
    a first column of electrodes, and a second column of electrodes extending alongside the first column of electrodes, each of the first and second columns of electrodes including at least a first electrode separated from a second electrode by an insulative spacer, and each of the first and second columns of electrodes having a length that is defined from a proximal end of the respective first electrode to a distal end of the respective second electrode;
    an expandable member disposed between the first and second columns of electrodes; and
    an expansion mechanism adapted to transmit externally applied pressure to expand the expandable member, the expansion of the expandable member forcing each of the first column of electrodes and the second column of electrodes into a respective position in which the first and second columns of electrodes are spaced apart from one another and the length of the first column extends approximately parallel with the length of the second column; and
    wherein the first column of electrodes is coupled to a first body, the first body including a distal tip; and
    the second column of electrodes is coupled to a second body, the second body including a distal tip unattached to the first body distal tip, such that, when the first and second columns of electrodes are in the spaced apart position, the first body distal tip is spaced apart from the second body distal tip.

12. The system of claim 11, wherein the expandable member extends along an entirety of the length of each of the first and second columns of electrodes.

13. The system of claim 12, wherein:
    the expandable member comprises an inflatable chamber; and
    the expansion mechanism comprises an inflation medium.

14. The system of claim 12, wherein:
    the expandable member includes a first end and a second end and extends between the first end and the second end; and
    the expansion mechanism comprises an elongate member adapted to bring the first end of the expandable member closer to the second end of the expandable member to expand the member.

15. The system of claim 12, further comprising a sidewall surrounding a lumen, the lumen extending proximally from the expandable member and providing a passageway for the transmission of externally applied pressure.

16. The system of claim 15, further comprising:
a body extending proximally from one of the first and second columns of electrodes; and
wherein the sidewall surrounding the lumen is a part of the body.

17. The system of claim 15, further comprising:
a body extending proximally from one of the first and second columns of electrodes; and
wherein the sidewall surrounding the lumen is separate from the body.

18. The system of claim 12, further comprising a body extending proximally from both the first and second columns of electrodes, the body including a lumen extending proximally from the expandable member and providing a passageway for the transmission of externally applied pressure.

19. The system of claim 12, wherein the expandable member comprises a first expandable member, and further comprising:
a second expandable member extending alongside the first column of electrodes and being offset from the first expandable member about a perimeter of the first column of electrodes; and
a third expandable member extending alongside the second column of electrodes and being offset from the first expandable member about a perimeter of the second column of electrodes; and
wherein the expansion mechanism is further adapted to transmit externally applied pressure to expand the second and third expandable members.

20. The system of claim 11, wherein the expandable member extends alongside at least a portion of the length of each of the first and second columns of electrodes.

21. The system of claim 11, wherein:
the expandable member comprises an inflatable chamber; and
the expansion mechanism comprises an inflation medium.

22. The system of claim 11, wherein:
the expandable member includes a first end and a second end and extends between the first end and the second end; and
the expansion mechanism comprises an elongate member adapted to bring the first end of the expandable member closer to the second end of the expandable member to expand the member.

23. The system of claim 11, further comprising a sidewall surrounding a lumen, the lumen extending proximally from the expandable member and providing a passageway for the transmission of externally applied pressure.

24. The system of claim 23, further comprising:
a body extending proximally from one of the first and second columns of electrodes; and
wherein the sidewall surrounding the lumen is a part of the body.

25. The system of claim 23, further comprising:
a body extending proximally from one of the first and second columns of electrodes; and
wherein the sidewall surrounding the lumen is separate from the body.

26. The system of claim 11, further comprising a body extending proximally from both the first and second columns of electrodes, the body including a lumen extending proximally from the expandable member and providing a passageway for the transmission of externally applied pressure.

27. A medical system for electrical stimulation, the system comprising:
a first column of electrodes, and a second column of electrodes extending alongside the first column of electrodes, each of the first and second columns of electrodes including at least a first electrode separated from a second electrode by an insulative spacer;
an expandable area extending between the first and second columns of electrodes, the expandable area formed by a sidewall attached to each of the first and second columns of electrodes; and
an expansion element adapted for insertion within the expandable area in order to force the first column of electrodes apart from the second column of electrodes, when the expansion element is expanded within the area; and
wherein the first column of electrodes is coupled to a first body, the first body including a distal tip; and
the second column of electrodes is coupled to a second body, the second body including a distal tip unattached to the first body distal tip, such that, when the first column of electrodes is forced apart from the second column of electrodes, the first body distal tip is also forced apart from the second body distal tip.

28. The system of claim 27, wherein the expansion element comprises an inflatable member, an inflation medium, and an inflation device coupled thereto.

29. The system of claim 27, wherein the expansion element comprises an expandable member and an elongate member adapted to bring a first end of the expandable member closer to a second end of the expandable member to expand the expansion element.

30. The system of claim 27, further comprising another sidewall surrounding a lumen, the lumen extending proximally from the expandable area and providing a passageway for the expansion element.

31. The system of claim 30, further comprising:
a body extending proximally from one of the first and second columns of electrodes; and
wherein the sidewall surrounding the lumen is a part of the body.

32. The system of claim 30, further comprising:
a body extending proximally from one of the first and second columns of electrodes; and
wherein the sidewall surrounding the lumen is separate from the body.

33. The system of claim 27, further comprising a body extending proximally from both the first and second columns of electrodes, the body including a lumen extending proximally from the expandable area and providing a passageway for the expansion element.

34. A medical system for electrical stimulation, the system comprising:
a first body including a distal tip;
a second body including a distal tip, the second body distal tip being unattached to the first body distal tip;
a first column of electrodes coupled to the first body in proximity to the first body distal tip, and a second column of electrodes coupled to the second body in proximity to the second body distal tip, the second column of electrodes extending alongside the first column of electrodes, and each of the first and second columns of electrodes including at least a first electrode separated from a second electrode by an insulative spacer;
an expandable member disposed between the first and second columns of electrodes; and
an expansion mechanism adapted to transmit externally applied pressure to expand the expandable member, the expansion of the expandable member forcing the first column of electrodes and the first body distal tip apart from the second column of electrodes and the second body distal tip.

35. The system of claim 34, wherein:
each of the first and second columns of electrodes has a length that is defined from a proximal end of the respective first electrode to a distal end of the respective second electrode; and
the expandable member extends along an entirety of the length of each of the first and second columns of electrodes.

36. The system of claim 34, wherein the expandable member extends alongside at least a portion of each of the first and second columns of electrodes.

37. The system of claim 34, wherein:
the expandable member comprises an inflatable chamber; and
the expansion mechanism comprises an inflation medium.

38. The system of claim 34, wherein:
the expandable member extends between a first end thereof and a second end thereof; and
the expansion mechanism comprises an elongate member adapted to bring the first end of the expandable member closer to the second end of the expandable member to expand the member.

39. The system of claim 34, further comprising a sidewall surrounding a lumen, the lumen extending proximally from the expandable member and providing a passageway for the transmission of externally applied pressure.

40. The system of claim 34, wherein each of the first and second bodies includes a proximal end; and further comprising another body coupled to each of the first and second body proximal ends and extending proximally therefrom.

41. The system of claim 40, wherein the other body includes a lumen extending proximally from the expandable member and providing a passageway for the transmission of externally applied pressure.

42. The system of claim 34, further comprising:
a first connector assembly and a second connector assembly; and
wherein the first body extends proximally from the first column of electrodes to the first connector assembly; and
the second body extends proximally from the second column of electrodes to the second connector assembly.

43. The system of claim 42, wherein one of the first and second bodies includes a lumen extending proximally from the expandable member and providing a passageway for the transmission of externally applied pressure.

44. The system of claim 42, further comprising a sidewall surrounding a lumen, the sidewall being separate from the first and second bodies, and the lumen extending proximally from the expandable member and providing a passageway for the transmission of externally applied pressure.

45. The system of claim 34, further comprising:
another expandable member extending alongside at least one of the first and second columns of electrodes; and
wherein the expansion mechanism is further adapted to transmit externally applied pressure to expand the other expandable member.

* * * * *